US00PP29348P3

(12) United States Plant Patent
Danziger

(10) Patent No.: US PP29,348 P3
(45) Date of Patent: May 29, 2018

(54) ***BIDENS* PLANT NAMED 'DBIDGOLDEM'**

(50) Latin Name: *Bidens ferulifolia*
Varietal Denomination: DBIDGOLDEM

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/330,420

(22) Filed: Sep. 19, 2016

(65) Prior Publication Data

US 2018/0084702 P1 Mar. 22, 2018

(51) Int. Cl.
*A01H 5/02* (2018.01)

(52) U.S. Cl.
USPC ..... Plt./410
CPC ..... *A01H 5/025* (2013.01)

(58) Field of Classification Search
USPC ..... Plt./410
CPC ..... A01H 5/025; A01H 5/02; A01H 5/00
See application file for complete search history.

(56) References Cited

PUBLICATIONS

Germania Seed Company Welby Gardens—Hardy starts vegetative annuals perennials geraniums and Regal geranium Program 79, retrieved on Sep. 14, 2017, retrieved from the Internet at https://www.germaniaseed.com/pdf/2017/779_welby.pdf pp. 1-2 and 28. (Year: 2016).*

Upov Pluto Plant Variety Database Sep. 9, 2017 *Bidens* Dbidgoldem, retrieved on Sep. 14, 2017, retrieved from the Internet at https://www3.wipo.int/pluto/user/en/index.jsp 1 page (Year: 2017).*

* cited by examiner

*Primary Examiner* — June Hwu
(74) *Attorney, Agent, or Firm* — Cassandra Bright

(57) ABSTRACT

A new and distinct *Bidens* cultivar named 'DBIDGOLDEM' is disclosed, characterized by well-branched plant with an upright growth habit and medium height. Foliage is dark green. Flowers are solitary, large, golden colored with eight petals. The new variety is a *Bidens*, normally produced as an outdoor garden or container plant.

2 Drawing Sheets

Figure 1:
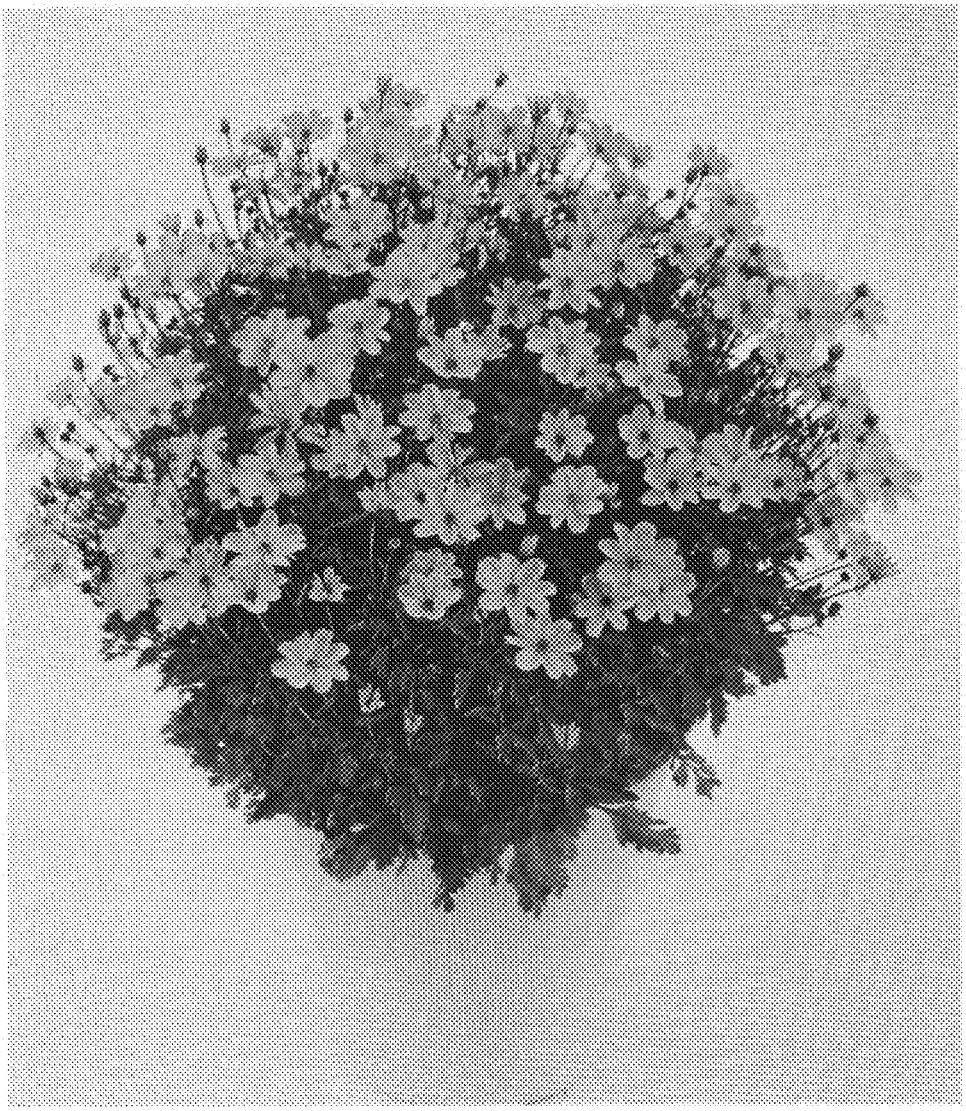

Latin name of the genus and species: *Bidens ferulifolia.*
Variety denomination: 'DBIDGOLDEM'.

BACKGROUND OF THE INVENTION

The new *Bidens* cultivar is a product of a planned breeding program conducted by the inventor, Gavriel Danziger in Moshav Mishmar Hashiva, Israel. The open pollination resulting in this new variety was made during June of 2013.

The seed parent is the unpatented, propriety variety referred to as *Bidens* 'cv.12-1593'. The pollen parent is unknown as it was an open pollination breeding program. The new variety was discovered in July of 2012 by the inventor in a group of seedlings resulting from the 2012 open pollination, in a greenhouse in Moshav Mishmar Hashiva, Israel.

Asexual reproduction of the new cultivar 'DBIDGOLDEM' was first performed by vegetative terminal cuttings during September of 2012, at a greenhouse in Moshav Mishmar Hashiva, Israel. Subsequent propagation by vegetative cuttings has shown that the unique features of this cultivar are stable and reproduced true to type in more than 25 successive generations.

SUMMARY OF THE INVENTION

The cultivar 'DBIDGOLDEM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBIDGOLDEM' These characteristics in combination distinguish 'DBIDGOLDEM' as a new and distinct *Bidens* cultivar:

1. Upright growth habit.
2. Very well branched plant habit.
3. Medium height.
4. Large, single golden flowers with six to eight petals.
5. Dark green foliage.

PARENT COMPARISON

Plants of the new cultivar 'DBIDGOLDEM' are similar to plants of the seed parent, most horticultural characteristics, however, plants of the new cultivar 'DBIDGOLDEM' differ in the following;

1. Plant habit of the new variety is upright whereas the seed parent is a mounded plant.
2. New variety produces more branches than the parent variety.
3. Parent is taller than new variety.
4. Parent has smaller, semi-double golden flowers, whereas the new cultivar has larger flowers with a single whorl of petals.
5. New cultivar has dark green foliage whereas the parent has grey-green foliage.

COMMERCIAL COMPARISON

Plants of the new cultivar 'DBIDGOLDEM' can be compared to the unpatented commercial variety *Bidens* 'DANYEL0'. These varieties are similar in most horticultural characteristics; however, 'DBIDGOLDEM' differs in the following:

1. The new variety has an upright growth habit, whereas the comparator has a mounded habit.
2. The new variety has less branches than the comparator.
3. The comparator variety is compact and short, the new variety has medium height.
4. Comparator variety has extra-large yellow flowers, the new variety has a large golden flower.
5. Comparator variety has lighter green foliage than the new variety.

Plants of the new cultivar 'DBIDGOLDEM' can also be compared to the unpatented commercial variety *Bidens* 'DANYEL10'. These varieties are similar in most horticultural characteristics; however, 'DBIDGOLDEM' differs in the following:

1. The new variety has an upright growth habit, whereas the comparator has a semi-trailing growth habit.
2. The new variety is less branched than the comparator.
3. The comparator variety is compact and short, the new variety has medium height.
4. Comparator variety has extra-large, semi-double yellow flowers, the new variety has single, large golden flowers.
5. Comparator variety has lighter green foliage than the new variety.

BRIEF DESCRIPTION OF THE PHOTOGRAPHS

The accompanying photograph in FIG. 1 illustrates in full color a typical plant of 'DBIDGOLDEM' grown in 12 cm pots outdoors, in Moshav Mishmar Hashiva, Israel.

Figure 2:
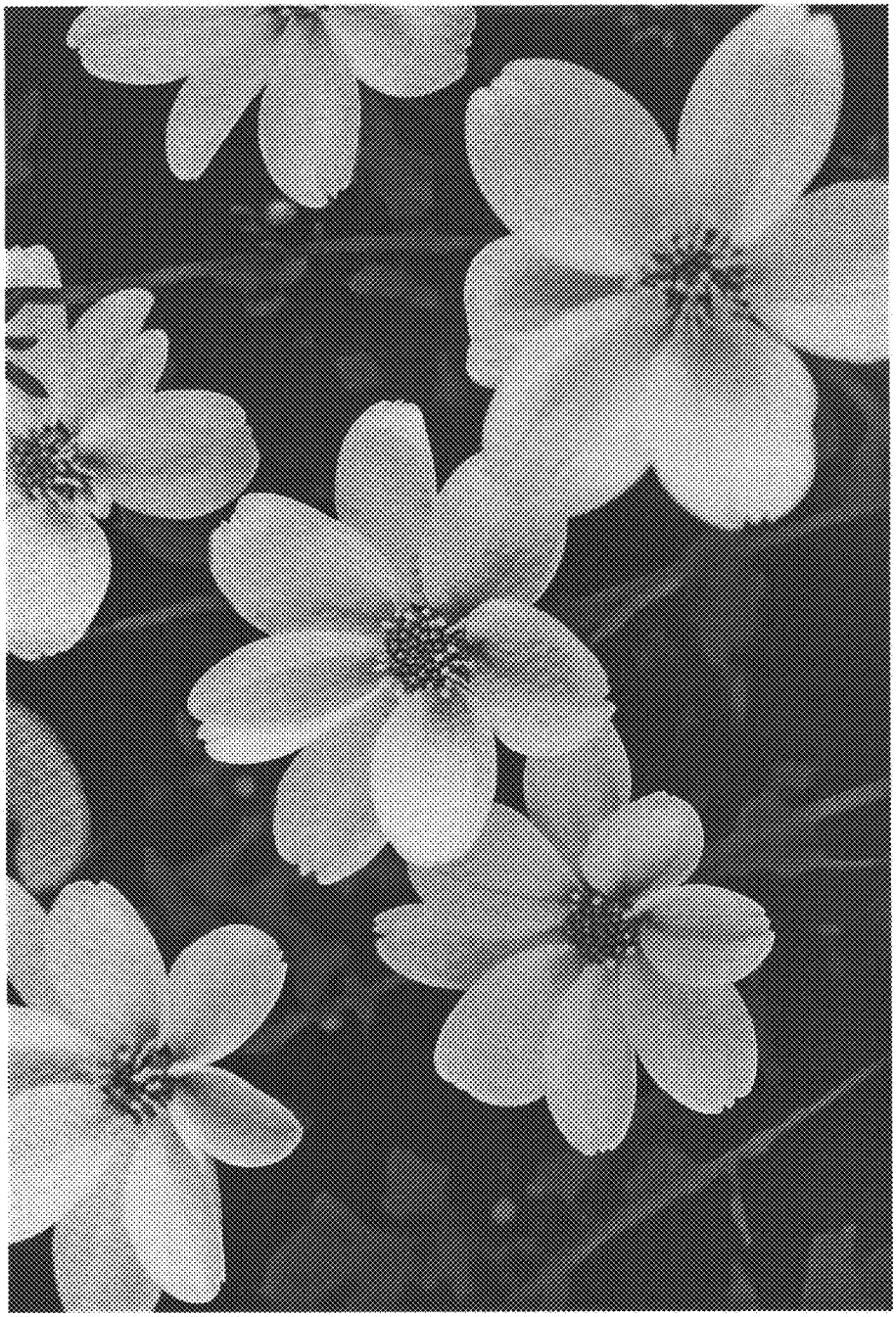

FIG. 2 illustrates in full color a close up view of flowers of 'DBIDGOLDEM'. Age of the plant photographed is approximately 11 weeks from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color comparators are made to The Royal Horticultural Society Mini Colour Chart 2005 except where general terms of ordinary dictionary significance are used. The following observations and measurements describe 'DBIDGOLDEM' plants grown in a greenhouse and outdoors in Moshav Mishmar Hashiva, Israel, under natural lighting. Measurements were taken during April of 2016. The plants were approximately 120 days old from a rooted cutting in a 20 cm pot. The growing temperature ranged from approximately 20° C. to 35° C. during the days, 17° C. to 23° C. during the nights. Measurements and numerical values represent averages of typical plant types.

Botanical classification: *Bidens ferulifolia* 'DBIDGOLDEM'.

Propagation:

*Time to initiate rooting.*—10 to 14 days at approximately 20° C.

*Root description.*—Fibrous.

Plant:

*Growth habit.*—Upright.

*Height.*—Approximately 30 cm.

*Plant spread.*—Approximately 25 cm.

*Growth rate.*—Medium.

*Branching characteristics.*—Well branched.

*Length of lateral branches.*—Approximately 25 cm.

*Diameter of lateral branches.*—Approximately 0.3 cm.

*Texture of lateral branches.*—Glabrous.

*Internodes length.*—Approximately 2.0 cm.

*Strength of stem.*—Strong.

*Color of lateral branches.*—Near Yellow-Green group 148B.

*Angle of branches.*—Approximately 30°.

*Number of leaves per lateral branch.*—Approximately 8.

Foliage:

*Leaf.*—Arrangement: Opposite. Average Length: Approximately 5.5 cm. Average Width: Approximately 3.0 cm. Shape of blade: Bipinnate and pinnate foliage present, on same plant at similar maturity levels. Apex: Acute. Base: Cuneate. Attachment: approximately 45°. Margin: Lobed. Texture of top surface: Slightly pubescent. Texture of bottom surface: Glabrous. Appearance top surface: Matte. Appearance bottom surface: Matte. Leaf Internode length: Approximately 0.7 cm. Color: Young foliage upper side: Near Green N137B. Young foliage under side: Near Green 147B. Mature foliage upper side: Near Green N137A. Mature foliage under side: Near Green 147B. Venation: Type: Pinnate. Venation color upper side: Near Green 137C. Venation color under side: Near Green 147B.

*Petiole.*—Length: 1.5 cm. Diameter: 0.2 cm. Pubescence: None. Color: Near Green 147B.

Flower:

*Bloom period.*—Year-round.

*Bud.*—Bud shape: Rounded. Bud length: Approximately 1.0 cm. Bud diameter: Approximately 0.8 cm. Bud color: Near RHS Yellow-Orange 17A.

*Inflorescence.*—Form: Solitary flower.

*Flower.*—Diameter of entire flower: Approximately 4.0 cm. Depth of flower: Approximately 1.0 cm. Diameter of disc: Approximately 0.8 cm. Depth of disc: Approximately 0.6 cm.

*Ray florets.*—Number of Ray Florets: Average of 6 to 8. Length: Approximately 1.5 cm. Width: Approximately 0.8 cm. Apex shape: Notched. Margin: Entire.

*Color.*—Ray Florets Upper surface at first opening: Near Yellow-Orange 17A. Upper surface at maturity: Near Yellow-Orange 17B. Upper surface at fading: Near Yellow-Orange 17C. Under surface at first opening: Near Yellow-Orange 17C. Under surface at maturity: Near Yellow-Orange 17C. Under surface at fading: Near Yellow-Orange 17C.

*Disc florets.*—Number of Disc Florets: Approximately 30. Length: Approximately 0.5 cm. Width: Approximately 0.1 cm. Shape: Linear. Margin: Entire. Color At first opening: Near Yellow-Orange 17A. At maturity: Near Yellow-Orange 17B. At fading: Near Yellow-Orange 17B.

*Fragrance.*—Slightly sweet.

*Phyllaries/involucral bracts.*—Number: 10. Sepal length: Approximately 0.5 cm. Sepal width: Approximately 0.1 cm. Sepal texture: Slightly pubescent. Apex shape: Acute. Margin: Entire. Color: Near Green N137B.

*Peduncle.*—Pedicel length: Approximately 5.0 cm. Pedicel diameter: Approximately 0.2 cm. Angle: Approximately 30° from center of whorl. Color: Near Yellow-Green 144B. Strength: Flexible. Pedicel texture: Glabrous.

Reproductive organs:

*Disc florets.*—Androecium: Stamens: 5. Anther shape: Rounded. Anther length: Approximately 0.1 cm. Anther color: Near RHS Brown 200B. Pollen quantity: sparse. Gynoecium: Pistil number: 1. Pistil shape: Linear. Pistil length: Approx. 0.4 cm. Style length: Approx. 0.1 cm. Style color: Near Green-Yellow 1C. Stigma shape: Two-lobed. Stigma color: Near Yellow-Orange 23A. Ovary diameter: 0.05 cm. Ovary color: Near Green-Yellow 1D.

*Ray florets.*—No reproductive structures present.

Other characteristics:

*Seeds and fruits.*—Shape: Needle-like. Color: Near RHS Brown 200A. Size: Approximately 0.6 cm.

*Disease/pest resistance.*—Typical to other *Bidens* varieties.

*Temperature tolerance.*—Temperature range: 5° C. to 40° C.

*Drought tolerance.*—Not tolerant to drought.

What is claimed is:

1. A new and distinct cultivar of *Bidens* plant named 'DBIDGOLDEM' as herein illustrated and described.

* * * * *